United States Patent
Mennen

(10) Patent No.: US 6,730,811 B1
(45) Date of Patent: May 4, 2004

(54) PROCESS FOR THE PREPARATION OF UREA

(75) Inventor: Johannes H. Mennen, Roggel (NL)

(73) Assignee: DSM N.V., Heerlen (NL)

( * ) Notice: Subject to any disclaimer, the term of this patent is extended or adjusted under 35 U.S.C. 154(b) by 799 days.

(21) Appl. No.: 09/586,606

(22) Filed: Jun. 2, 2000

Related U.S. Application Data

(63) Continuation of application No. PCT/NL98/00677, filed on Nov. 30, 1998.

(30) Foreign Application Priority Data

Dec. 5, 1997 (NL) ............................................. 1007713

(51) Int. Cl.$^7$ ............................................ C07C 273/04
(52) U.S. Cl. ............................. 564/70; 564/66; 564/67; 564/71; 564/72; 422/188
(58) Field of Search .............................. 564/66, 67, 70, 564/71, 72; 422/188

(56) References Cited

U.S. PATENT DOCUMENTS

| | | | |
|---|---|---|---|
| 4,613,696 A | 9/1986 | Zardi | 564/67 |
| 4,684,194 A | 8/1987 | Jenkins et al. | 439/260 |
| 5,763,660 A | 6/1998 | Rescalli | 564/70 |

*Primary Examiner*—Peter O'Sullivan
(74) *Attorney, Agent, or Firm*—Pillsbury Winthrop LLP

(57) ABSTRACT

The invention relates to a process for the preparation of urea from ammonia and carbon dioxide in which the low-pressure carbamate stream formed in the further upgrading of the urea synthesis solution is stripped in a $CO_2$-carbamate stripper in countercurrent contact with $CO_2$, which results in the formation of a gas mixture consisting substantially of ammonia and carbon dioxide.

Figure 1:
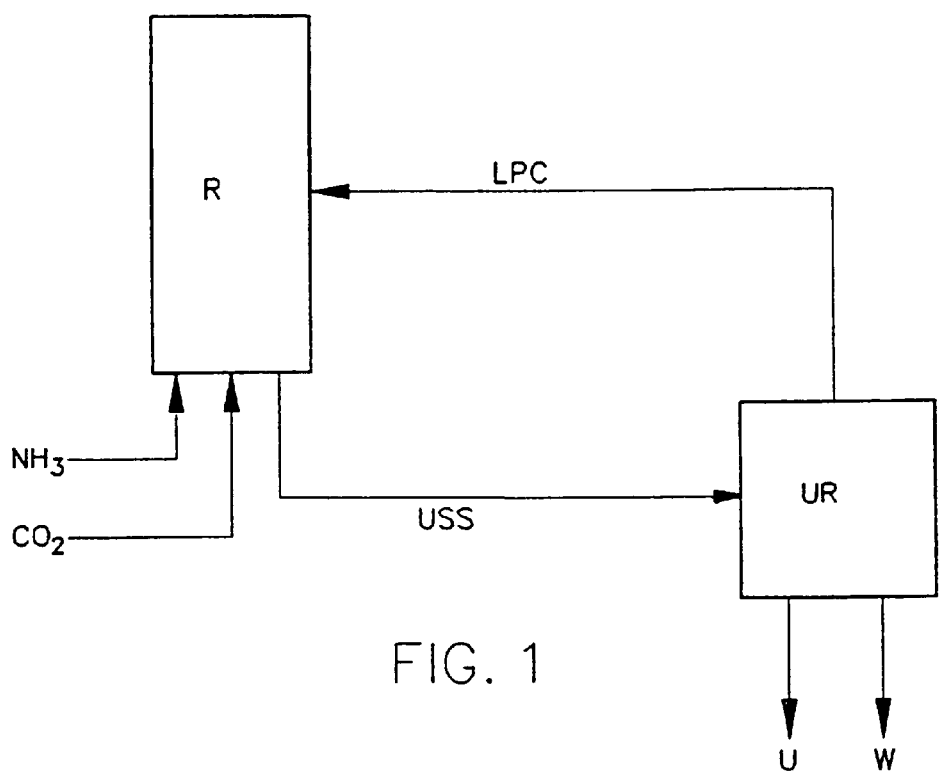

This gas mixture is preferably subsequently condensed in a high-pressure carbamate condenser and then returned to the synthesis zone.

14 Claims, 6 Drawing Sheets

PROCESS FOR THE PREPARATION OF UREA

This application is a continuation of PCT/NL98/00677, filed Nov. 30, 1998.

The invention relates to a process for the preparation of urea from ammonia and carbon dioxide.

Urea can be prepared by introducing ammonia and carbon dioxide into a synthesis zone at a suitable pressure (for example 12–40 MPa) and a suitable temperature (for example 160–250° C.), which first results in the formation of ammonium carbamate according to the reaction:

$$2NH_3 + CO_2 \rightarrow H_2N-CO-ONH_4$$

Dehydration then causes the ammonium carbamate formed to form urea according to the equilibrium reaction:

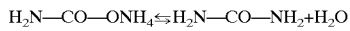

$$H_2N-CO-ONH_4 \leftrightarrows H_2N-CO-NH_2 + H_2O$$

The degree to which this last conversion proceeds depends on, among other factors, the temperature and the ammonia excess used. As the reaction product a solution is obtained that consists substantially of urea, water, ammonium carbamate and unbound ammonia. The ammonium carbamate and the ammonia must be removed from the solution and are preferably returned to the synthesis zone. In addition to the aforementioned solution, a gas mixture is formed in the synthesis zone, which consists of non-converted ammonia and carbon dioxide plus inert gases. Ammonia and carbon dioxide are removed from this gas mixture and are preferably also returned to the synthesis zone. The synthesis zone may comprise separate zones for the formation of ammonium carbamate and urea. These zones may however also be united in a single apparatus.

In practice, different methods are used for the preparation of urea. At first urea was prepared in so-called conventional high-pressure urea plants, which were at the end of the 1960s however succeeded by processes carried out in so-called urea stripping plants.

A conventional high-pressure urea plant is understood to be a urea plant in which the decomposition of the ammonium carbamate not converted into urea and the expulsion of the usual ammonia excess take place at a substantially lower pressure than the pressure in the synthesis reactor itself. In a conventional high-pressure urea plant the synthesis reactor is usually operated at a temperature of 180–250° C. and a pressure of 15–40 MPa. In a conventional high-pressure urea plant the reactants not converted into urea are, after expansion, dissociation and condensation at a pressure of between 1.5 and 10 Mpa, returned to the urea synthesis as a carbamate stream. In addition, in a conventional high-pressure urea plant ammonia and carbon dioxide are fed directly to the urea reactor. The molar $NH_3/CO_2$ ratio (=N/C ratio) in the urea synthesis lies between 3 and 5 in a conventional high-pressure urea process.

These conventional urea plants were initially designed as so-called once-through processes, in which the non-converted ammonia was neutralized with acid (for example nitric acid) and converted into ammonium salts (for example ammonium nitrate). Major disadvantages of this process were this large amount of ammonium salt and the low degree of $CO_2$ conversion. These conventional once-through urea processes were soon replaced by the so-called conventional recycle processes, in which all the non-converted ammonia and carbon dioxide are returned to the urea reactor. This recycling is carried out in two steps. A first recycling step at a medium pressure (1.8–2.5 MPa) and a second recycling step at a low pressure (0.2–0.5 MPa). In the first recycling step the urea synthesis solution coming from the reactor is heated in a heater, upon which ammonium carbamate decomposes into gaseous ammonia and carbon dioxide while further the excess ammonia also evaporates here. This gas mixture is subsequently converted into pure ammonia and a water-containing ammonium carbamate stream in a rectifying column. Both streams are returned to the urea reactor. In the second recycling step the urea solution from the first recycling step is reheated and then separated. The gas stream thus obtained is condensed and subsequently fed to the rectifying column of the first step. Next, urea is released from the urea solution coming from the second recycling step, in the evaporation at reduced pressure, through the evaporation of water. The two recycling steps and the evaporation together constitute the main part of the urea recovery.

A urea stripping plant is understood to be a urea plant in which the greater parts of the decomposition of the ammonium carbamate not converted into urea and the expulsion of the usual ammonia excess take place at a pressure that is essentially almost the same as the pressure in the synthesis reactor. This decomposition/expulsion takes place in a stripper, whether or not with the addition of a stripping medium. In a stripping process, carbon dioxide and/or ammonia can be used as stripping gas before these components are dosed to the reactor. This stripping takes place in a stripper placed downstream of the reactor, the solution coming from the urea reactor, which, in addition to urea, ammonium carbamate and water, also contains ammonia and carbon dioxide, being stripped with the stripping gas with the supply of heat. It is also possible to use thermal stripping here. Thermal stripping means that ammonium carbamate is decomposed and the ammonia and carbon dioxide present are removed from the urea solution exclusively by means of the supply of heat. The gas stream containing ammonia and carbon dioxide that is released from the stripper is returned to the reactor via a high-pressure carbamate condenser.

The gas mixture that has not reacted in the urea synthesis is removed from the synthesis section via a blow-down stream. In addition to the condensable ammonia and carbon dioxide, this gas mixture (synthesis off-gas) also contains inert gases such as, for example, nitrogen, oxygen and optionally hydrogen. These inert gases derive from the raw materials and from the make-up air in the carbon dioxide feed to the synthesis to protect the materials from corrosion. This gas stream is blown down from the synthesis section for example downstream of the reactor or downstream of the high-pressure carbamate condensation, depending on the process route chosen. It is however preferable to absorb the condensable components (ammonia and carbon dioxide) in a high-pressure scrubber at synthesis pressure before the inert gases are blown down. In such a high-pressure scrubber the condensable components, ammonia and carbon dioxide, are absorbed from the synthesis off-gas into the low-pressure carbamate stream formed in the further upgrading. This scrubbing process in the high-pressure scrubber can be stimulated by using a heat exchanger that extracts heat from the process. The carbamate stream from the high-pressure scrubber, which contains the ammonia and carbon dioxide absorbed from the synthesis off-gas, is returned to the synthesis via the high-pressure carbamate condenser. The reactor, high-pressure scrubber, stripper and high-pressure carbamate condenser are the most important parts of the high-pressure section of a urea stripping plant.

In a urea stripping plant the synthesis reactor is operated at a temperature of 160–240° C. and preferably at a temperature of 170–220° C. The pressure in the synthesis reactor is 12–21 MPA, preferably 12.5–19 MPa. The N/C ratio in the synthesis in a stripping plant lies between 2.5 and 4. The synthesis can be carried out in one or two reactors. When use is made of two reactors, the first reactor can be operated using virtually fresh raw materials and the second using raw materials entirely or partly recycled, for example from the urea recovery.

A frequently used embodiment for the preparation of urea according to a stripping process is the Stamicarbon® $CO_2$-stripping process described in European Chemical News, Urea Supplement, of Jan. 17, 1969, pages 17–20. In this process the urea synthesis solution formed in the synthesis zone at a high pressure and temperature is subjected to a stripping treatment at synthesis pressure by bringing the solution into countercurrent contact with gaseous carbon dioxide while heat is being supplied. This causes the greater part of the ammonium carbamate present in the solution to be decomposed into ammonia and carbon dioxide. These decomposition products are expelled from the solution in gaseous form and are discharged together with a small amount of water vapour and the carbon dioxide used for the stripping. Besides with the aid of carbon dioxide, as described in this publication, such a stripping treatment can also be carried out thermally or using gaseous ammonia as the stripping gas, or using a mixture of the aforementioned gases. The greater part of the gas mixture obtained in the stripping treatment is condensed and adsorbed in a high-pressure carbamate condenser, after which the ammonium carbamate formed is returned to the synthesis zone for the formation of urea. The stripping of the urea synthesis solution with a stripping medium can take place in more than one stripper.

The high-pressure carbamate condenser can for example be designed as a so-called submerged condenser as described in NL-A-8400839. The gas mixture to be condensed is then introduced into the shell-side space of a shell-and-tube heat exchanger, into which space a diluted carbamate solution coming from the high-pressure scrubber is also introduced. The heat of dissolution and condensation then released is discharged with the aid of a medium flowing through tubes, for example water, which is in the process converted into low-pressure steam. The submerged condenser can be placed horizontally or vertically. It is however particularly advantageous to carry out the condensation in a horizontally placed submerged condenser (a so-called pool condenser; see for example Nitrogen No 222, July–August 1996, pp. 29–31), because, in comparison with other embodiments of this condenser, the liquid generally has a longer residence time in the pool condenser. This results in the formation of extra urea, which raises the boiling point, so that the difference in temperature between the carbamate solution containing urea and the cooling medium increases, resulting in better heat transfer.

After the stripping treatment, the pressure of the stripped urea synthesis solution is reduced in the urea recovery and the solution is evaporated, after which urea is released. This urea recovery is carried out in one or more pressure steps, depending on the degree to which carbamate has already been expelled in the stripper(s). This produces a low-pressure carbamate stream in the recovery. This low-pressure carbamate stream is returned via the high-pressure scrubber to the section operating at synthesis pressure. In the high-pressure scrubber this low-pressure carbamate stream scrubs non-converted ammonia and carbon dioxide from the gas mixture blown down from the section operating at synthesis pressure to remove the non-condensable gases from the synthesis section.

The theoretically feasible degree of conversion of ammonia and carbon dioxide into urea is determined by the thermodynamic position of the equilibrium and depends on for example the $NH_3/CO_2$ ratio, the $H_2O/CO_2$ ratio and the temperature and can be calculated using the models for example described in Bull. of the Chem. Soc. of Japan 1972, vol. 45, pp. 1339–1345, and J. Applied Chem. of the USSR (1981), vol. 54, pp. 1898–1901.

The conversion of ammonium carbamate into urea and water in the reactor can be effected by ensuring a sufficiently long residence time of the reaction mixture in the reactor. The residence time will generally be more than 10 min., preferably more than 20 min. The residence time will generally be shorter than 2 hours, preferably shorter than 1 hour. Preferably the residence time of the urea synthesis solution in the reactor is chosen so that at least 90% of the theoretically feasible amount of urea is prepared, in particular more than 95%. At a higher temperature and pressure in the reactor a shorter residence time is often sufficient for obtaining a high degree of conversion.

The conversion of ammonium carbamate into urea is an equilibrium reaction whose position is adversely influenced by the water present in the reactor.

An important source of water is the low-pressure carbamate stream which is formed during the further upgrading of the urea synthesis solution and which is fed to the synthesis zone via the high-pressure scrubber in a $CO_2$ stripping plant as described above. In a conventional urea plant this low-pressure carbamate stream can be fed directly to the reactor. This carbamate stream has a high water content and is disadvantageous for the conversion of ammonia and carbon dioxide into urea. This carbamate stream is, however, an important source of raw materials, which is why recycling of this carbamate stream to the synthesis zone is nevertheless opted for in urea plants. A further disadvantage of this carbamate stream with its high water content is its corrosive character at a high temperature. This imposes high demands on the quality of all the pipes and equipment operating at synthesis pressure.

The degree of $CO_2$ conversion is used as a measure of the degree of conversion of ammonia and carbon dioxide into urea. In urea stripping plants this degree usually lies between 58 and 62% and in conventional urea plants between 64 and 68%.

With the present invention it has been found that the degree of $CO_2$ conversion can be substantially increased by stripping the low-pressure carbamate stream formed during the further upgrading of the urea synthesis solution in countercurrent contact with $CO_2$ in a $CO_2$ carbamate stripper, which results in a gas mixture consisting substantially of ammonia and carbon dioxide.

This gas mixture is preferably subsequently condensed in a high-pressure carbamate condenser and then returned to the synthesis zone.

In a urea stripping plant the condensation of carbamate can preferably take place in the high-pressure carbamate condenser already present. In a conventional urea plant the gas mixture formed is returned from the $CO_2$-carbamate stripper to the synthesis, but is preferably condensed in a high-pressure carbamate condenser to be additionally installed, after which it is returned to the synthesis.

It is also preferable to supply the ammonia feed to this high-pressure carbamate condenser and transfer it to the synthesis together with the carbamate stream. In both the conventional urea plants and the urea stripping plants low-pressure steam is produced in this high-pressure carbamate condenser, which can be used in the downstream processing.

The advantage of this is that the steam consumption in a conventional urea plant decreases substantially.

In addition to the gas mixture, consisting substantially of ammonia and carbon dioxide, a liquid phase with a high water content is formed in the $CO_2$-carbamate stripper. The reactants ammonia, ammonium carbamate and carbon dioxide can be removed from this liquid phase with a high water content for example through a reduction in pressure and further purification by means of steam stripping in for example the urea recovery.

The separation of the low-pressure ammonium carbamate stream into a gas phase and a liquid phase with a high water content is also described in WO 96/23767 and EP-A-727414. In these publications the separation is however not effected in an additionally installed carbamate stripper in which the low-pressure ammonium carbamate stream is stripped with the aid of carbon dioxide, but by supplying heat. The advantage of stripping with $CO_2$ in an additionally installed $CO_2$-carbamate stripper is that, because of the stripping with $CO_2$, during the separation of the low-pressure carbamate stream into a gas phase and a liquid phase with a high water content, the process conditions are much milder than in the separation through the supply of heat as used in the aforementioned publications. These much milder conditions are advantageous in selecting materials in connection with corrosion. Cheaper types of steel can then be used. Feeding the low-pressure carbamate stream to the existing stripper in a urea stripping plant presents the drawback that no use is made of the smaller amount of urea synthesis solution that has to be stripped and hence no saving in high-pressure steam is achieved.

Any type of stripper can be used as the $CO_2$-carbamate stripper. Preferably use is made of a stripper based on the countercurrent principle. In particular use is made of a stripper of the same type as the $CO_2$ stripper in the aforementioned Stamicarbon $CO_2$-stripping process. The pressure in the $CO_2$-carbamate stripper is virtually identical to the pressure in the urea synthesis. In conventional urea plants the pressure in the $CO_2$-carbamate stripper may preferably vary between 15 and 40 MPa. In urea stripping plants the pressure may preferably vary between 12.5 and 19 MPa. In both a conventional urea plant and a urea stripping plant the temperature at the top of the $CO_2$-carbamate stripper usually lies below 270° C., preferably below 240° C. The temperature usually lies above 120° C., in particular above 150° C. The residence time of the low-pressure carbamate stream in the $CO_2$-carbamate stripper is short, being less than 10 minutes, in particular less than 5 minutes.

Using an additional $CO_2$-carbamate stripper means that use is made of the absorbing capacity of the low-pressure carbamate stream from the urea recovery in the high-pressure scrubber of a urea stripping plant, while it is simultaneously ensured that no excess water is fed to the synthesis section. This ensures that, in the scrubber, ammonia and carbon dioxide are removed from the gas mixture to be blown down from the synthesis section (containing the non-condensable components). The use of the low-pressure carbamate stream presents the advantage that the absorption in the high-pressure scrubber is optimal because of this carbamate stream's low vapour pressure. This carbamate stream has a vapour pressure that corresponds to the vapour pressure of the urea recovery and lies between 0.2 and 2.5 Mpa, which is much lower than the synthesis pressure, which lies between 12.5 and 19 MPa. In this process an inert stream is moreover obtained from the high-pressure scrubber, which contains fewer traces of ammonia and carbon dioxide, as a result of which the further off-gas purification that is often necessary in view of environmental requirements will cost less.

A second advantage in a urea stripping plant is that better absorption takes place in the high-pressure scrubber of a stripping plant, as a result of which the inerts content in the reactor off-gas can be reduced. This enables a higher temperature at the same pressure in the synthesis zone, as a result of which the yield becomes higher and less energy is consumed. It is also possible to operate the reactor at the same temperature but at a lower pressure, and this also presents an energy advantage in bringing the ammonia and carbon dioxide to the required pressure.

The water stream coming from the $CO_2$-carbamate stripper contains only little ammonia and carbon dioxide. This water stream can be returned to the urea recovery, where these components are removed from the water stream via a desorption step and are added to the low-pressure carbamate stream after condensation in a condenser. The water stream from the $CO_2$-carbamate stripper can be given some residence time under synthesis conditions before it is returned to the recovery. The result is that still some urea formation takes place at the prevailing synthesis pressure and he corresponding temperature. This water is then transferred to the recovery, where this urea is recovered.

It has been found that a degree of $CO_2$ conversion of more than 70% is achieved in urea stripping plants with the process according to the present invention, which implies a substantial increase in the urea plant's capacity. In conventional urea plants, too, a degree of $CO_2$ conversion that approaches the equilibrium is achieved with the present invention.

It has also been found that by stripping with carbon dioxide it is possible to avoid the need to use very high temperatures in this carbamate stripper as would be the case if the separation into a gas stream and a liquid stream with a high water content were to be effected exclusively by supplying heat. This presents the advantage that corrosion problems due to the aggressiveness of ammonium carbamate at high temperatures are avoided.

It has furthermore been found that this process is very suitable for improving and optimizing existing urea plants. This invention leads to a reduction of approximately 20% in the load on the existing stripper, the high-pressure carbamate condenser and the subsequent recovery section(s) in urea stripping plants. The load on the recovery sections of conventional urea plants is also substantially decreased as a result of this invention. Both conventional urea plants and urea stripping plants can be debottlenecked at only low costs and with very good results by additionally installing a $CO_2$-carbamate stripper.

The invention hence also relates to a method for improving and optimizing an existing urea stripping plant with a high-pressure scrubber. This can be effected by installing a $CO_2$-carbamate stripper between the high-pressure scrubber and the high-pressure carbamate condenser. The invention further relates to a method for improving and optimizing a urea plant without a high-pressure scrubber. This can be effected by installing a $CO_2$-carbamate stripper directly after the urea recovery for stripping of the low-pressure ammonium carbamate stream with $CO_2$. It is in these processes however preferable to additionally install a high-pressure scrubber at the point where the inerts-containing synthesis off-gas stream leaves the synthesis section, and to use the low-pressure carbamate stream as a scrubbing liquid in it. The carbamate stream coming from the high-pressure scrubber can then be fed to the $CO_2$-carbamate stripper. This carbamate stream is stripped in the $CO_2$-carbamate stripper, after which the carbamate gases that are virtually free of water are fed directly, or preferably via a high-pressure carbamate condenser, to the synthesis section.

The invention also relates to a method for improving and optimizing conventional urea plants. This can be effected by installing a $CO_2$-carbamate stripper directly after the urea recovery, after which the gas stream from the $CO_2$-carbamate stripper is condensed in an additionally installed high-pressure carbamate condenser.

The invention further relates to a second method for improving and optimizing an existing conventional urea plant. This can be effected by additionally installing a high-pressure scrubber, a $CO_2$-carbamate stripper and a high-pressure carbamate condenser.

The invention is hence suitable for use in all existing urea processes, both conventional urea processes and urea stripping processes. Examples of conventional urea processes in which the invention can be used are:

Urea Technologies Inc. (UTI); Heat Recycle Process (HRP);
Mitsui Toatsu Corporation; Conventional Process of Toyo Engineering Corporation;
Vulcan; Once-Through Urea Process.

Examples of Urea Stripping Processes in Which the Invention can be Used are:

Stamicarbon; $CO_2$-Stripping Process;
Snamprogetti; Ammonia-Stripping Process;
Snamprogetti; Self-stripping Process;
Toyo Engineering Corporation; ACES Process (Advanced process for Cost and Energy Saving);
Montedison; Isobaric-Double-Recycle (IDR) process;
Urea Casale SA; HEC process.

Of the urea processes mentioned above the urea stripping processes of Stamicarbon, Toyo-ACES and IDR have a high-pressure scrubber. In this high-pressure scrubber the synthesis off-gas from the reactor is incorporated in the low-pressure carbamate stream coming from the urea recovery. In these processes the $CO_2$-carbamate stripper is preferably installed directly after the high-pressure scrubber.

In urea processes without a high-pressure scrubber, such as the Snamprogetti, UTI and Urea Casale processes, the $CO_2$-carbamate stripper is installed directly after the urea recovery. In these processes it is however preferable, as already indicated above, to additionally install a high-pressure scrubber at the point where the inerts-containing synthesis off-gas stream leaves the synthesis section, and to use the low-pressure carbamate stream as a scrubbing liquid in it. The carbamate stream leaving the high-pressure scrubber can then be fed to the $CO_2$-carbamate stripper. In the $CO_2$-carbamate stripper this carbamate stream is then stripped with $CO_2$, after which the carbamate off-gases which are virtually free of water are fed directly, or preferably via the high-pressure carbamate condenser, to the synthesis section. The water stream from the $CO_2$-carbamate stripper can be returned to the urea recovery.

Figure 3:
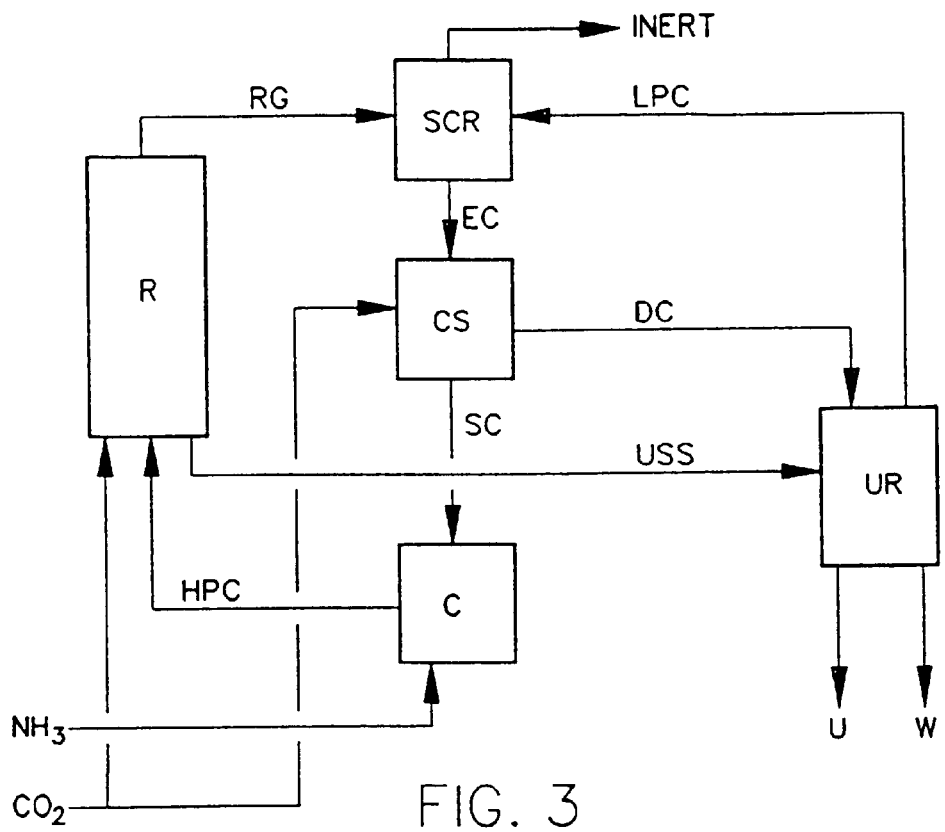
Figure 4:
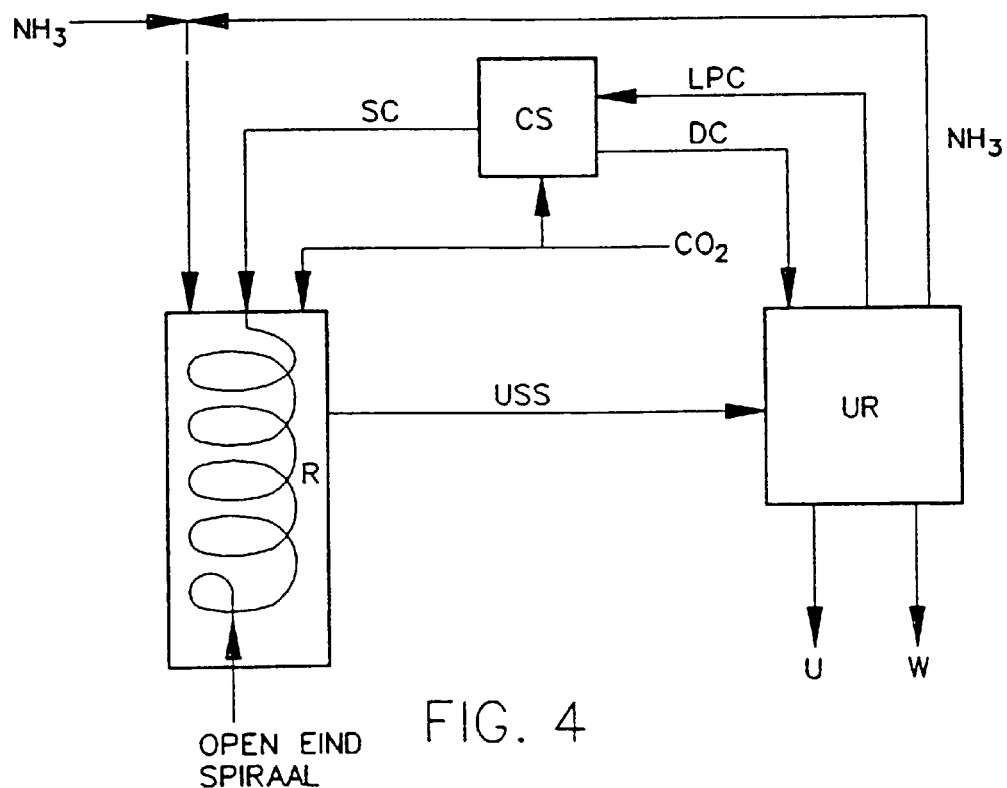
Figure 5:
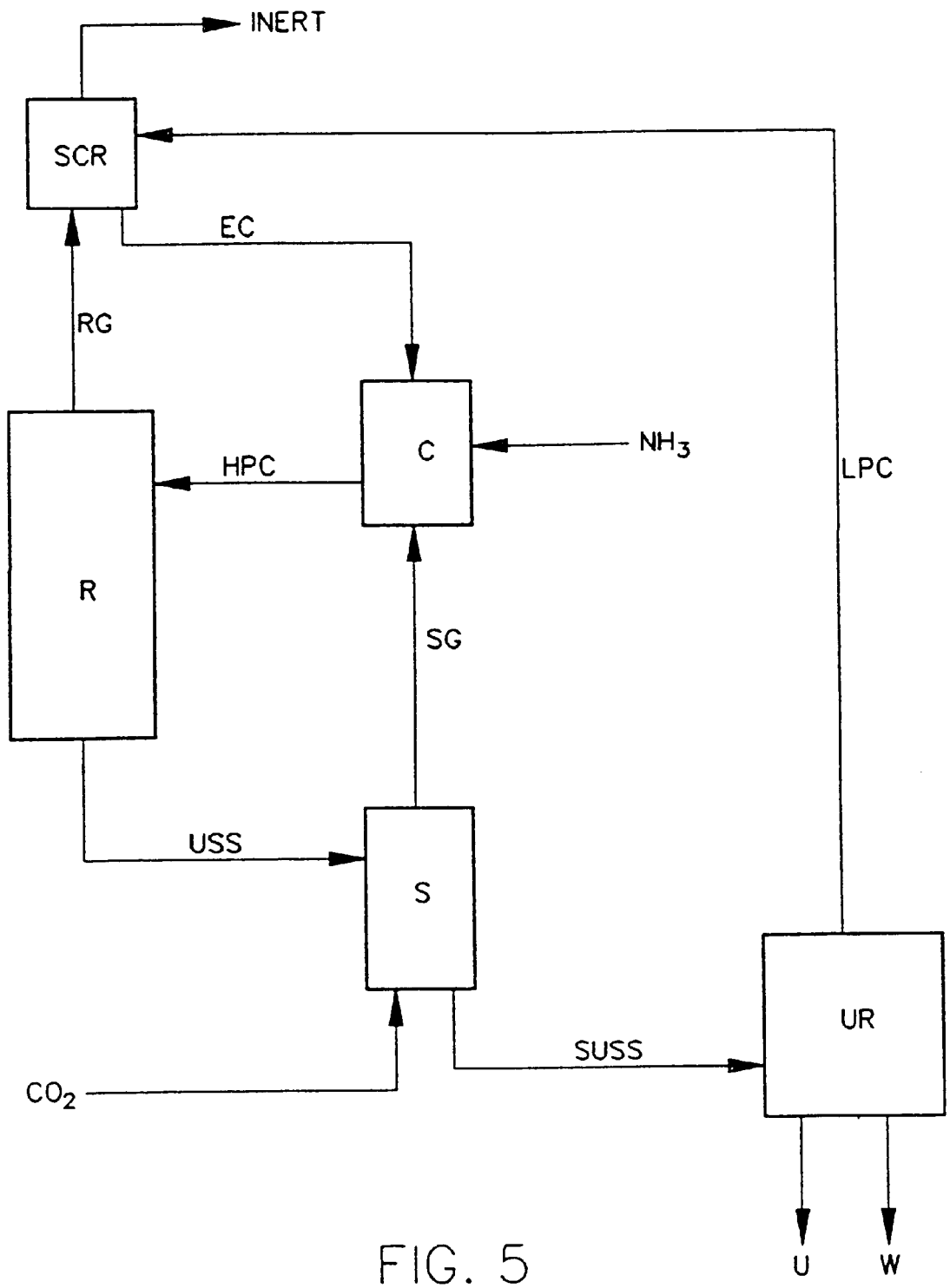

The invention will be further elucidated below by way of illustration with reference to the following figures, of which FIGS. 1 and 5 represent the state of the art and FIGS. 2, 3, 4, 6, 7 and 8 are embodiments of the present invention.

FIG. 1: Part of a conventional urea plant without a $CO_2$-carbamate stripper

Figure 2:
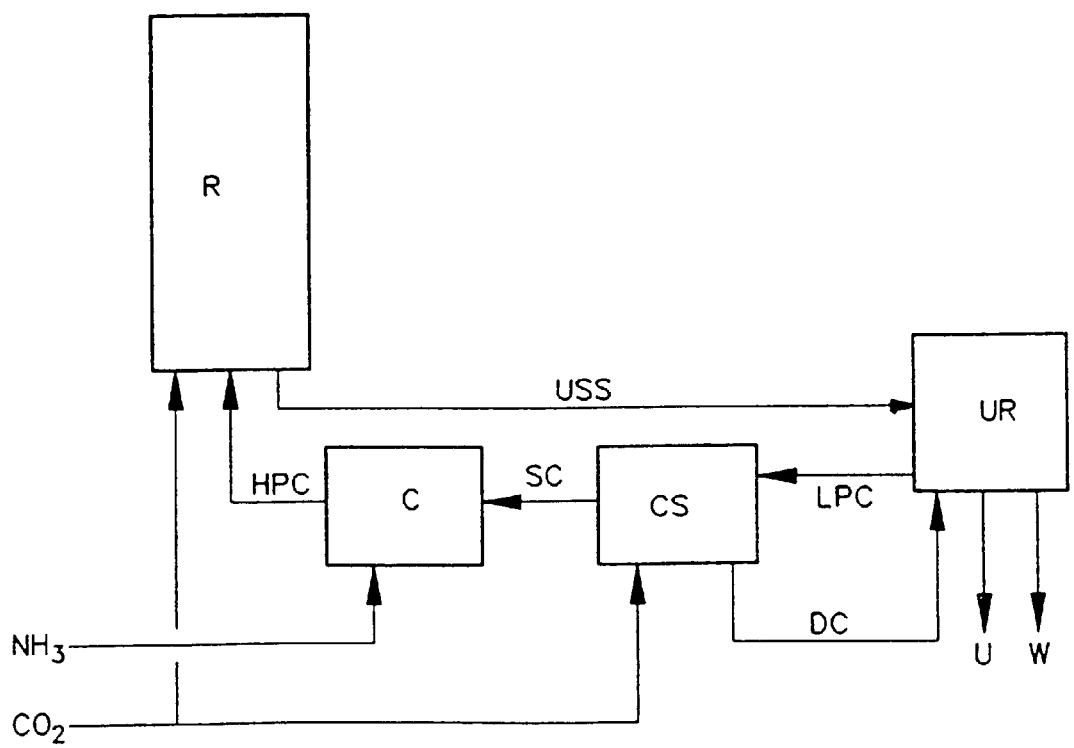

FIG. 2: Part of a conventional urea plant with a $CO_2$-carbamate stripper and a high-pressure carbamate condenser FIG. 3: Part of a conventional urea plant with a $CO_2$-carbamate stripper, high-pressure carbamate condenser and high-pressure scrubber FIG. 4: Part of a conventional urea plant according to the UTI process with a $CO_2$-carbamate stripper FIG. 5: Part of a urea stripping plant according to the Stamicarbon $CO_2$-stripping process without a $CO_2$-carbamate stripper FIG. 6: Part of a urea stripping plant according to the Stamicarbon $CO_2$-stripping process with a $CO_2$-carbamate stripper FIG. 7: Part of a urea stripping plant according to the TEC-ACES process with a $CO_2$-carbamate stripper FIG. 8: Part of a urea plant according to the Snamprogetti self-stripping process with a $CO_2$-carbamate stripper and a high-pressure scrubber.

In these figures the same symbols are used for corresponding parts and corresponding streams. FIGS. 2,3,4,6,7 and 8 present the various preferred embodiments by way of illustration. Other embodiments in which the ammonium carbamate stream of reduced pressure is stripped with carbon dioxide in an additional $CO_2$-carbamate stripper are also possible.

In FIG. 1 R represents a urea reactor in a conventional urea plant, to which ammonia and carbon dioxide are supplied. From the reactor comes the urea synthesis solution (USS), which is fed to the urea recovery (UR). In the UR urea (U) is released and a water stream (W) and a low-pressure ammonium carbamate stream (LPC) are formed. This LPC is returned to the reactor.

FIG. 2 represents an embodiment of the invention used in a conventional urea plant. R represents the urea reactor to which a portion of the carbon dioxide is supplied. The urea synthesis solution (USS) is transferred to the urea recovery (UR), where urea (U) is released and water (W) is discharged. The low-pressure ammonium carbamate stream (LPC) formed in the UR is fed to a $CO_2$-carbamate stripper (CS), in which the LPC is stripped with carbon dioxide. The stripped LPC is fed to the reactor as a gas mixture consisting substantially of ammonia and carbon dioxide (SC) together with the ammonia feed via a high-pressure carbamate condenser. The diluted aqueous carbamate solution (DC) formed in the CS is recycled to the urea recovery (UR).

FIG. 3 schematically represents the conventional urea plant of FIG. 2 in which a high-pressure scrubber (SCR) has been additionally installed. Here the synthesis off-gas from the reaction section (RG) is incorporated in the low-pressure ammonium carbamate stream (LPC) from the urea recovery (UR). The enriched carbamate stream (EC) is fed from the high-pressure scrubber to the $CO_2$-carbamate stripper (CS), where it is stripped with $CO_2$.

FIG. 4 schematically represents one possible way of installing a $CO_2$-carbamate stripper (CS) in a conventional urea plant according to the UTI process. The CS has been installed between the urea recovery (UR) and the urea reactor (R). The urea synthesis solution (USS) is fed to the urea recovery (UR), where urea (U) is released and where water (W), ammonia and a low-pressure ammonium carbamate stream (LPC) are formed. The LPC is stripped with carbon dioxide in the CS, after which the resulting gas stream (SC), consisting substantially of ammonia and carbon dioxide, is fed to the reactor. The aqueous carbamate stream (DC) is recycled to the urea recovery (UR).

In FIG. 5 R represents a reactor in a Stamicarbon $CO_2$-stripping plant in which carbon dioxide and ammonia are converted into urea. The urea synthesis solution (USS) coming from the reactor is fed to a $CO_2$ stripper, in which the USS is converted into a gas stream (SG) and a liquid stream (SUSS). The gas stream (SG) consists substantially of ammonia and carbon dioxide and the SUSS is the stripped USS. The stream containing the stripped urea synthesis solution SUSS is transferred to the urea recovery (UR), where urea (U) is released and water (W) is discharged. In the UR a low-pressure ammonium carbamate stream (LPC) is obtained, which is fed to the high-pressure scrubber (SCR). In this scrubber the LPC is brought into contact with the gas stream coming from the reactor (RG) which consists substantially of ammonia and carbon dioxide but which also contains the inert components (non-condensable components) present in the carbon dioxide feed and the ammonia feed. The enriched carbamate stream (EC) coming from the SCR is transferred to the high-pressure carbamate condenser (C), in which the SG stream is condensed with the aid of EC. The resulting high-pressure carbamate stream (HPC) is returned to the reactor. The fresh ammonia is in this example fed to the high-pressure carbamate condenser (C), but it can of course also be fed to a different point in the R→S→C→R loop or in the R→SCR→C→R loop.

Figure 6:
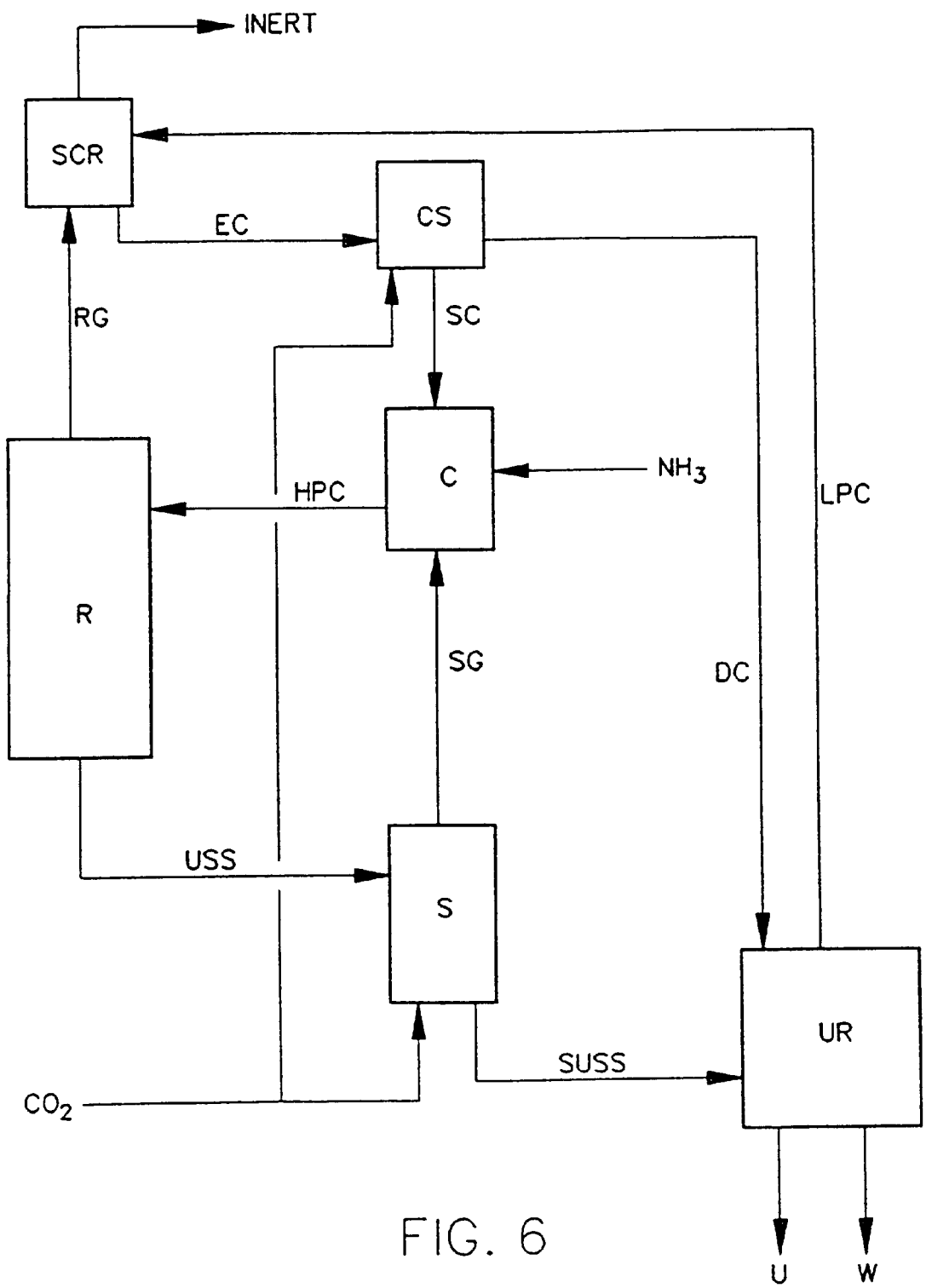

FIG. 6 schematically represents one possible way of incorporating an additional $CO_2$-carbamate stripper (CS) in a Stamicarbon $CO_2$-stripping plant. Here, a CS has been installed between the high-pressure scrubber (SCR) and the high-pressure carbamate condenser (C) in FIG. 5. In the CS the low-pressure ammonium carbamate stream (LPC) is stripped with carbon dioxide, after which the gases released (SC) are transferred to the high-pressure condenser (C). The carbamate stream with a high water content (DC) is recycled from the CS to the urea recovery.

Figure 7:
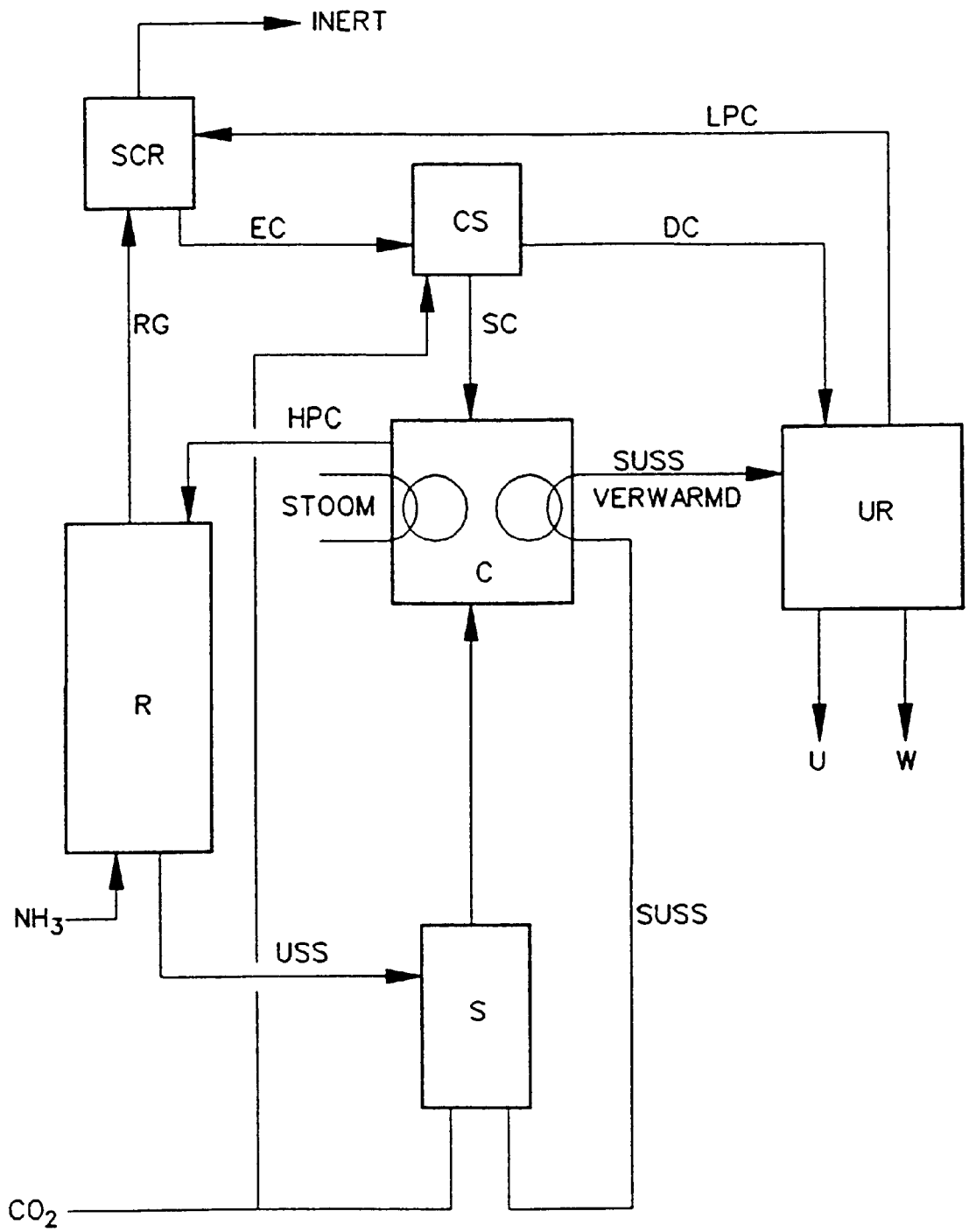

FIG. 7 schematically represents a urea process according to the TEC-ACES process, in which, by way of illustration, a $CO_2$-carbamate stripper has been installed between the high-pressure scrubber (SCR) and the high-pressure carbamate condenser (C). In this process the heat released in the high-pressure carbamate condenser (C) is used for direct heating of the urea synthesis solution (USS) treated in the stripper (S). The symbols in this figure represent parts of plants and streams as in FIG. 5.

Figure 8:
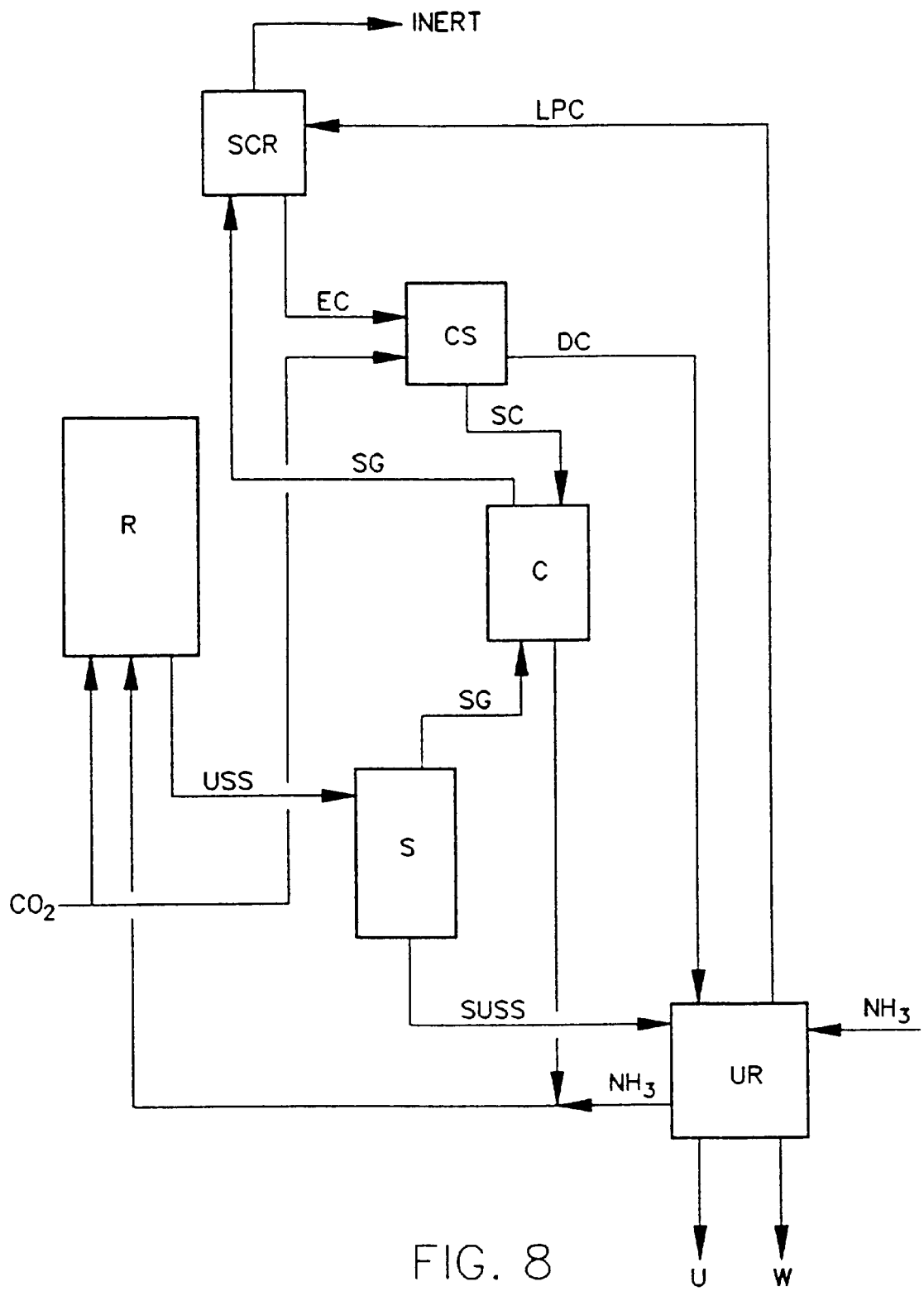

FIG. 8 shows a urea process according to the Snamprogetti Self-Stripping process in which a high-pressure scrubber (SCR) and a $CO_2$-carbamate stripper (SC) have additionally been included. The symbols again have the same meanings as in FIG. 5.

The invention will be further elucidated with reference to the following examples:

COMPARATIVE EXAMPLE A

Table 1 below indicates the compositions of the various streams in percent by weight for a Stamicarbon $CO_2$-stripping plant as indicated in FIG. 5. From the compositions of the streams a value of 58.5% follows for the degree of $CO_2$ conversion.

TABLE 1

Process streams in a Stamicarbon $CO_2$-stripping plant

| Stream | Urea | $NH_3$ | $CO_2$ | $H_2O$ | Inert |
|---|---|---|---|---|---|
| USS | 33.9 | 30.2 | 17.7 | 18.2 | — |
| $CO_2$ | — | — | 93.6 | 1.1 | 5.3 |
| SUSS | 55 | 7.8 | 10.2 | 27 | — |
| SG | — | 61.9 | 32.0 | 4.9 | 1.2 |
| $NH_3$ | — | 99.5 | — | 0.5 | — |
| HPC | — | 49.2 | 41.9 | 7.6 | 1.3 |
| RG | — | 68.6 | 21.0 | 4.4 | 6.0 |
| EC | — | 38.8 | 39.2 | 22.0 | — |
| LPC | — | 29.6 | 37.3 | 33.1 | — |
| Inert | — | 8.8 | 3.3 | — | 87.9 |

EXAMPLE I

Table 2 below gives the compositions of the various streams in percent by weight for a Stamicarbon $CO_2$-stripping plant in which a $CO_2$-carbamate stripper has additionally been installed as indicated in FIG. 6. From the compositions of the streams a value of 70.0% follows for the degree of $CO_2$ conversion.

TABLE 2

Process streams in a Stamicarbon $CO_2$-stripping plant with a $CO_2$-carbamate stripper

| Stream | Urea | $NH_3$ | $CO_2$ | $H_2O$ | Inert |
|---|---|---|---|---|---|
| USS | 43.8 | 28.3 | 13.8 | 14.1 | — |
| $CO_2$ | — | — | 93.6 | 1.1 | 5.3 |
| SUSS | 62.4 | 8.8 | 11.5 | 17.3 | — |
| SG | — | 60.0 | 31.5 | 7.0 | 1.5 |
| $NH_3$ | — | 99.5 | — | 0.5 | — |
| HPC | — | 50.2 | 42.6 | 6.2 | 1.0 |
| RG | — | 68.7 | 20.9 | 4.4 | 6.0 |
| EC | — | 38.2 | 39.1 | 22.7 | — |
| SC | — | 52.5 | 27.7 | 19.5 | 0.5 |
| LPC | — | 29.6 | 37.3 | 33.1 | — |
| DC | — | 7.9 | 10.2 | 81.9 | — |
| Inert | — | 8.8 | 3.3 | — | 87.9 |

The $CO_2$ stream to S is 81% and the $CO_2$ stream to CS is 19% of the total feed.

The flows of the various streams in Example I clearly differ from the flows of the corresponding streams in Comparative Example A. Table 3 below indicates the ratios of the flows of Example I and the flows of Comparative Example A.

TABLE 3

Ratios of the flows in Example I and Example A

| Stream | Ratio of the flows in Example I and Example A |
|---|---|
| USS | 0.78 |
| SUSS | 0.90 |
| SG | 0.70 |
| HPC | 0.83 |
| EC | 1.06 |
| LPC | 1.10 |

What is claimed is:

1. Process for the preparation of urea from ammonia and carbon dioxide, characterized in that the low-pressure carbamate stream formed during the further upgrading of the urea synthesis solution is stripped in a $CO_2$-carbamate stripper in countercurrent contact with $CO_2$, which results in a gas mixture consisting substantially of ammonia and carbon dioxide.

2. Process according to claim 1, wherein this gas mixture is condensed in a high-pressure carbamate condenser and is then returned to the synthesis zone.

3. Process according to claim 1, wherein in a urea stripping plant, the condensation of carbamate takes place in the high-pressure carbamate condenser already present.

4. Process according to claim 1, wherein in a conventional urea plant, the gas mixture formed from the $CO_2$-carbamate stripper is condensed in a high-pressure carbamate condenser to be additionally installed and is then returned to the synthesis.

5. Process according to claim 1, wherein a stripper that operates according to the countercurrent principle is used as the $CO_2$-carbamate stripper.

6. Process according to claim 5, wherein use is made of a $CO_2$-carbamate stripper of the same type as the $CO_2$ stripper in the aforementioned Stamicarbon $CO_2$-stripping process.

7. Process according to claim 5, wherein the pressure in the $CO_2$-carbamate stripper, used in a conventional urea plant, is between 15 and 40 MPa.

8. Process according to claim 5, wherein the pressure in the $CO_2$-carbamate stripper, used in a urea stripping plant, is between 12.5 and 19 MPa.

9. Process according to claim 4, wherein a high-pressure scrubber is additionally installed at the point where the inerts-containing synthesis off-gas stream leaves the synthesis section and using the low-pressure carbamate stream as a scrubbing liquid in it, after which the carbamate stream coming from the high-pressure scrubber is fed to the $CO_2$-carbamate stripper.

10. Method for improving and optimizing an existing urea stripping plant with a high-pressure scrubber by installing a $CO_2$-carbamate stripper between the high-pressure scrubber and the high-pressure carbamate condenser.

11. Method for improving and optimizing a urea plant without a high-pressure scrubber by installing a $CO_2$-carbamate stripper directly after the urea recovery for stripping with $CO_2$ of the low-pressure ammonium carbamate stream.

12. Method for improving and optimizing a urea plant without a high-pressure scrubber by installing a $CO_2$-carbamate stripper directly after the urea recovery for stripping with $CO_2$ of the low-pressure ammonium carbamate stream, a high-pressure scrubber having been additionally installed at the point where the inerts-containing synthesis off-gas stream leaves the synthesis section, and using the low-pressure carbamate stream as a scrubbing liquid in it, after which the carbamate stream coming from the high-pressure scrubber are fed to $CO_2$-carbamate stripper, after which this carbamate stream is stripped with $CO_2$ in this $CO_2$-carbamate stripper, after which the carbamate gases that are virtually free of water are fed directly, or via a high-pressure carbamate condenser, to the synthesis section.

13. Method for improving and optimizing conventional urea plants by installing a $CO_2$-carbamate stripper directly after the urea recovery, after which the gas stream from the $CO_2$-carbamate stripper is condensed in an additionally installed high-pressure carbamate condenser.

14. Method for improving and optimizing an existing conventional urea plant by additionally installing a high-pressure scrubber, a $CO_2$-carbamate stripper and a high-pressure carbamate condenser.

* * * * *